United States Patent [19]
Bowman et al.

[11] Patent Number: 5,335,666
[45] Date of Patent: Aug. 9, 1994

[54] MEDICAL MONITOR WITH INPUT REGULATION

[75] Inventors: Bruce R. Bowman, Eden Prairie; Peter Stasz, Mounds View, both of Minn.

[73] Assignee: Edentec, Eden Prairie, Minn.

[21] Appl. No.: 842,567

[22] Filed: Feb. 27, 1992

[51] Int. Cl.[5] .................................. A61B 5/08
[52] U.S. Cl. ........................ 128/723; 128/716
[58] Field of Search ............... 128/671, 696, 716, 720, 128/721, 723, 725

[56] References Cited
U.S. PATENT DOCUMENTS

| | | | |
|---|---|---|---|
| 4,305,400 | 12/1981 | Logan | 128/670 |
| 4,531,523 | 7/1985 | Anderson | 128/696 |
| 4,537,200 | 8/1985 | Widrow | 128/696 |
| 4,580,575 | 4/1986 | Birnbaum et al. | 128/723 |
| 4,781,201 | 11/1988 | Wright et al. | 128/696 |
| 4,803,997 | 2/1989 | Bowman | 128/723 |
| 4,890,630 | 1/1990 | Kroll et al. | 128/696 |
| 4,991,587 | 2/1991 | Blakeley et al. | 128/671 |
| 5,143,078 | 9/1992 | Mather et al. | 128/716 |
| 5,170,794 | 12/1992 | Reiche | 128/671 |

*Primary Examiner*—Lee S. Cohen
*Assistant Examiner*—Samuel Gilbert
*Attorney, Agent, or Firm*—Nawrocki, Rooney & Sivertson

[57] ABSTRACT

An apparatus for and method of monitoring respiration of a patient using impedance changes of the body to indicate respiration events. Cardiac related artifacts are suppressed by separately processing an EKG signal. Transient artifacts are accommodated by modifying the pass band of the respiration monitoring circuitry to selectively attenuate the signal within the frequency range of the transient artifact.

9 Claims, 8 Drawing Sheets

MEDICAL MONITOR WITH INPUT REGULATION

BACKGROUND OF THE INVENTION

1. Field of the Invention

The present invention generally relates to medical devices and more particularly relates to medical devices used to monitor patient respiration.

2. Description of the Prior Art

It has been known for some time that it is desirable to monitor patients to provide an alarm to attending personnel upon cessation of or the presence of grossly irregular respiration. Often monitoring devices are employed during the sleep of patients who are prone to central sleep apnea. Many of these patients are children or infants. An alarm condition indicates that remedial action is quickly needed to restore normal respiration before the patient suffers irreversible damage or death as a result of oxygen deficiency.

The early monitoring devices employed a number of sensor types to determine abnormal respiration. Sensors to measure airflow, blood gas composition, and stretching of the thorax have all been used with some degree of success. However, the most widely used monitoring technique in current clinical use measures changes of impedance across the thorax of a patient. This is accomplished by passing a small current through the thorax between two surface electrodes. As a patient inhales, the lungs fill with air, the thorax becomes less conductive, and the measured resistance across the thorax increases. Upon exhaling, the reverse happens, and the resistance decreases.

In the most practical systems, this small current is an alternating current having a frequency of 25-100 khz. By using this frequency range, the electrical circuitry can quite readily reject a number of noise components located on either side of the basic carrier frequency.

Through use of various signal processing techniques, considerable noise rejection is obtained. However, problems continue to exist with artifacts at or near the respiration rate. U.S. Pat. No 4,803,997, issued to Bowman and incorporated herein by reference, addresses the presence of an artifactual respiratory signal, which recurs at the basic heart rate of the patient, often referred to as cardiac artifact. In Bowman the cardiac artifact signal is explicitly sensed and processed using separate detection circuitry to ensure that the cardiac artifact is not treated as a respiration signal.

Rejection of the cardiac artifact using the Bowman invention provides a significant improvement. However, the cardiac artifact is periodic and recurring. Thus, that circuit is not completely effective in addressing artifacts caused by aperiodic and transient events such as motion of the patient. Such transient artifacts can cause swamping of the electronic circuitry, false indications of respiration, or both.

SUMMARY OF THE INVENTION

The present invention overcomes the disadvantages found in the prior art by providing a device for monitoring the respiration of a patient while offering enhanced rejection of transient artifacts. However, unlike most simple automatic gain control circuitry, the present invention tends to attenuate transient artifacts while having a minimal impact on respiration signal sensitivity.

Instead of changing only the gain within the pass band of the monitor under the presence of a transient artifact, the present invention changes the pass band of the monitor during the motion transient period as well. In this manner, maximum attenuation is achieved about the frequency of the artifact. Attenuation of the artifact tends to place the composite signal within the overall input limits of the monitor to permit the circuitry to operate within its normal range.

Because the large transient artifact is attenuated, the likelihood of the relatively small respiratory signals being swamped out, being missed by the monitor, and causing false alarms is greatly minimized. Similarly, because the potential respiration signal is not similarly attenuated, the monitoring circuitry maintains much of its sensitivity to an actual respiration event. This also minimizes the probability of a false alarm.

In the preferred mode, the present invention utilizes the cardiac artifact suppression technique of the above described Bowman system to deal with periodic artifacts, along with the pass band modification to accommodate transient artifacts. Preferably, the circuitry is implemented to cause the desired reaction and recovery times. This means that the attenuation occurs before the electronic circuitry is swamped by the potentially high amplitude transient artifact, and the monitor is returned to its normal gain and pass band as soon as the transient artifact has been completed. This substantially decreases that period of time during which the monitor may have its accuracy impaired by the presence of the transient artifact.

A key circuit element within the control circuit in the preferred embodiment is a photo resistor. As the incoming signal is sensed for the presence of a transient artifact, the intensity of the photo resistor lamp is increased in response thereto. The secondary of the photo resistor, which is located within the pass band and gain control circuit, changes resistance in accordance with changes of intensity of the lamp to control the pass band and attenuation. Thus the photo resistor provides isolation between the input and control circuits and also greatly improves response time to the beginning and end of a transient artifact.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
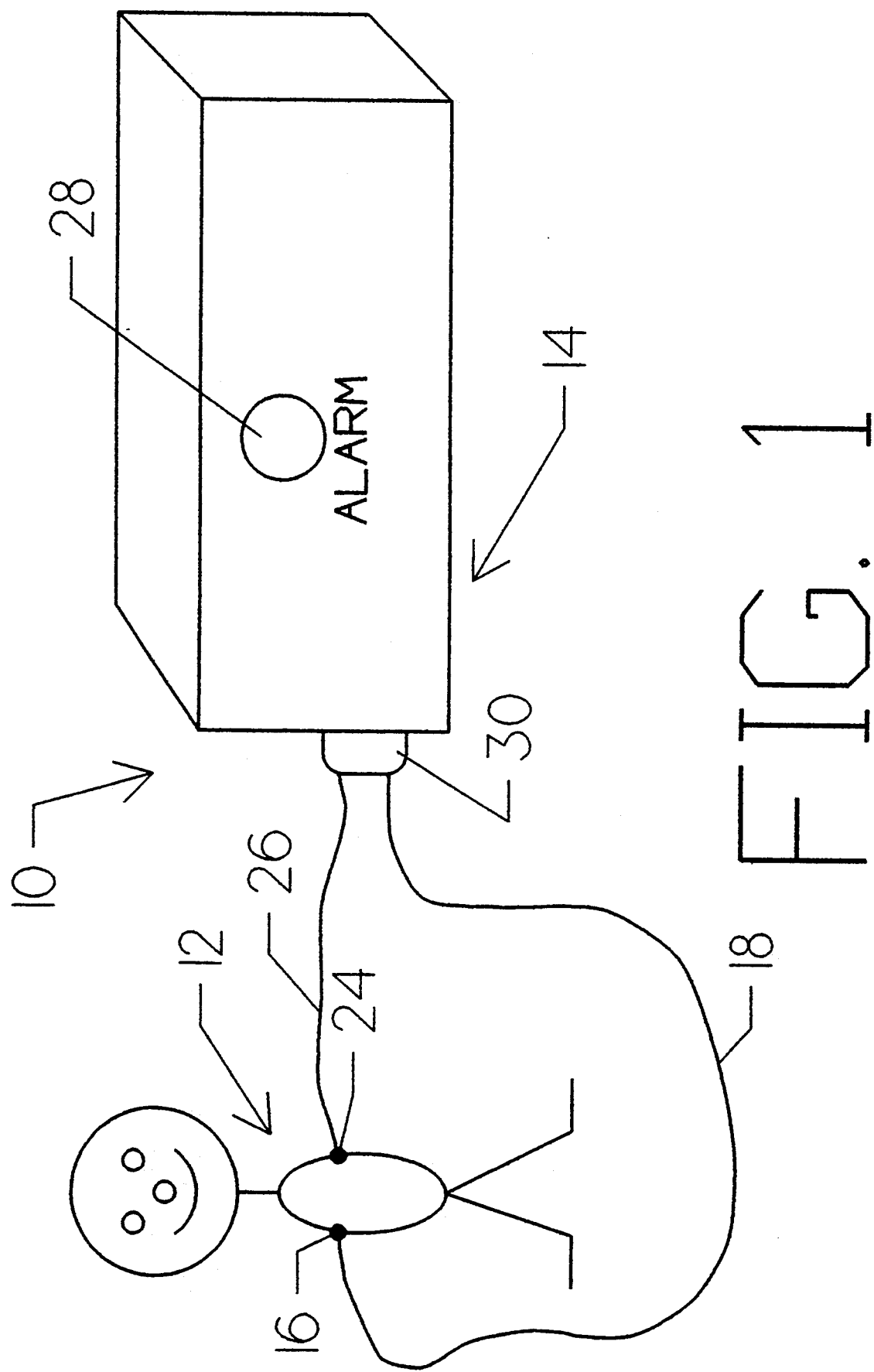
FIG. 1 is a schematic view of a medical monitor according to the present invention.

FIG. 1 is a basic schematic diagram of medical monitoring system 10 according to the present invention. This system is preferably similar to the EdenTec$^R$ Model 2000W monitoring system, except as specifically described herein. Patient 12 is normally coupled to medical monitoring system 10 during periods of sleep. Quite often, patient 12 is a child or infant.

Electrode 16 is coupled to the right chest of patient 12. It is electrically coupled to monitor 14 via conductor 18 and connector plug 30. Similarly, electrode 24 is coupled to the left chest and is electrically connected to monitor 14 with conductor 26 and connector plug 30. An optional reference electrode may be provided to monitor 14 through a separate conductor (not shown) and connector plug 30. The reference electrode can be placed over any electrically quiet location such as the right hip. Use of the reference electrode is not required with this circuitry.

To monitor respiration, an alternating current is passed between electrodes 16 and 24 across the thorax of patient 12. As the patient breaths, the effective resistance (i.e. impedance) changes between these electrodes. This change is measured by monitor 14.

Figure 2:
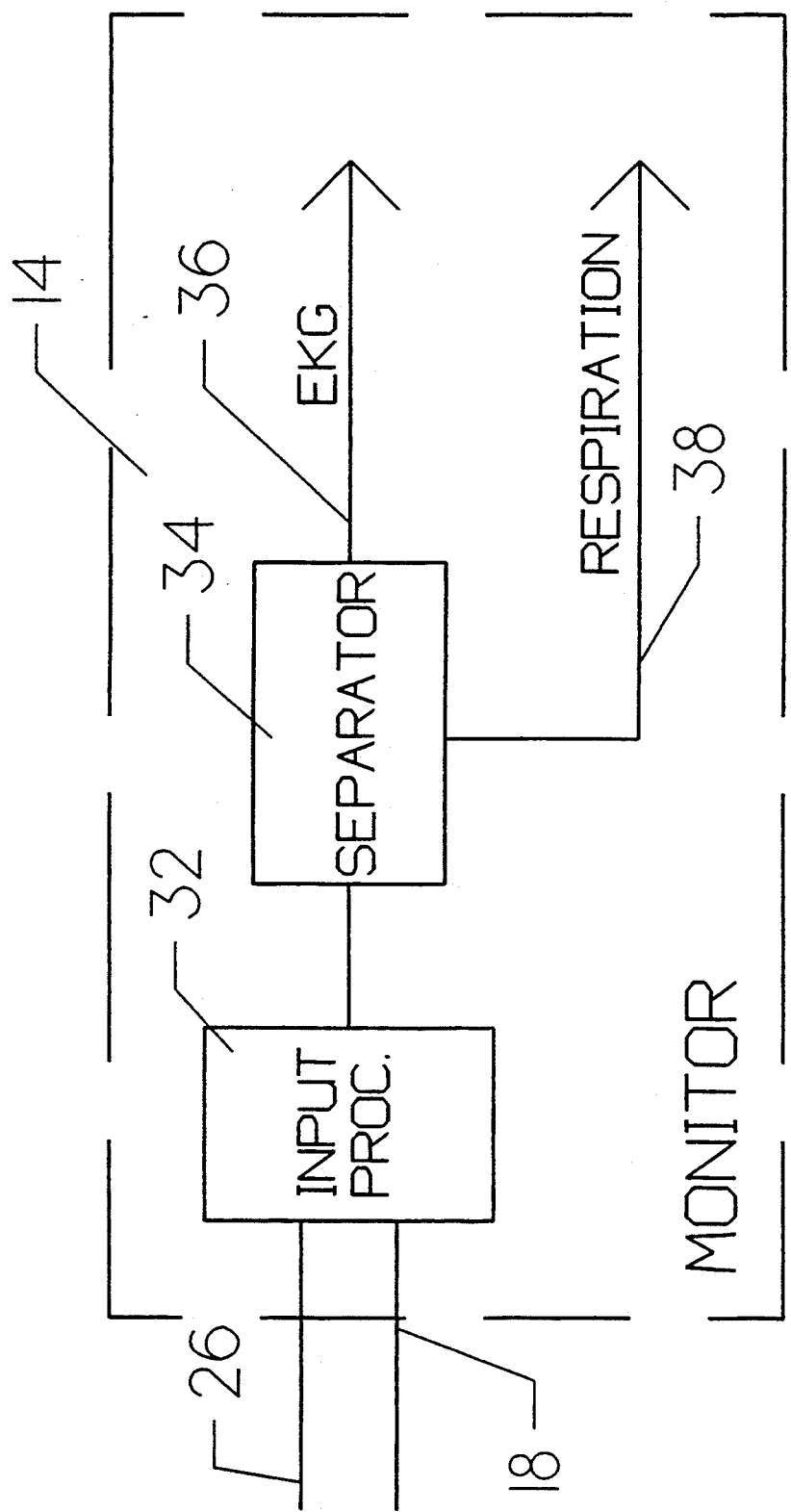
FIG. 2 is a block diagram of the medical monitor.

FIG. 2 is a basic block diagram of the operation of monitor 14. Conductors 18 and 26 are coupled to electrodes 16 and 24 respectively (see also FIG. 1). In normal operation these conductors will transfer signals representing respiration activity, cardiac activity (i.e. EKG), and transient artifacts. All of these signals are supplied to input processing circuitry 32 for amplification and band pass limiting.

Separator circuitry 34 separates the incoming signals into an EKG component which is sent by cable 36 for further processing and a respiration component which is sent by cable 38 for further processing. Separation is primarily accomplished by dividing the pass band of monitor 14 into a lower frequency component (i.e. EKG) and a higher frequency component (i.e. the drive frequency from which the respiration signal is extracted). The EKG signal is processed in accordance with the teachings of the above referenced Bowman reference. Further details of the respiration signal processing circuitry is provided below.

Figure 3:
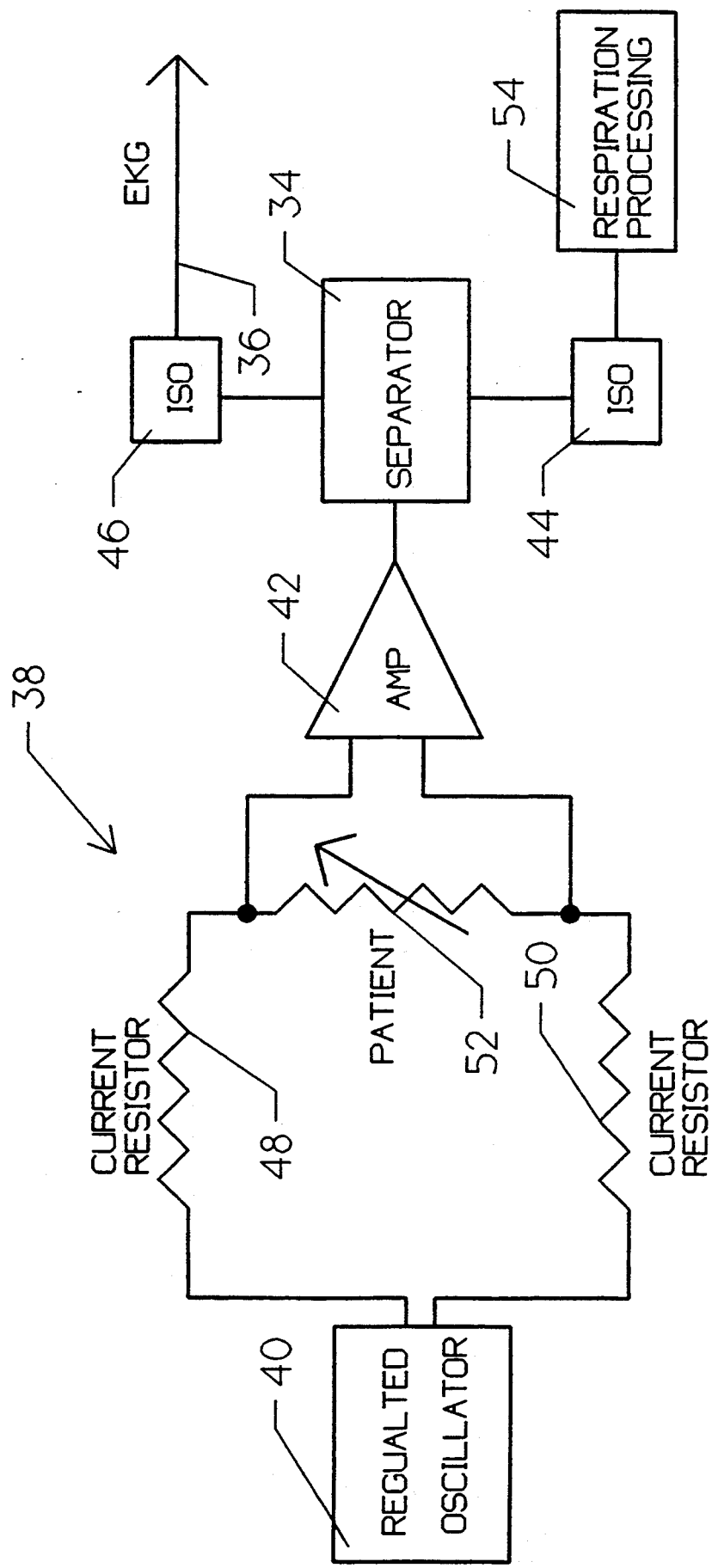
FIG. 3 is a basic schematic of the respiration monitor circuit.

FIG. 3 is a simplified schematic diagram 38 showing the operation of the respiration signal processing. Regulated oscillator 40 provides a regulated square wave alternating current output. Preferably this output has a frequency of 31.25 khz. The 31.25 khz signal proceeds through current resistor 48, patient 12 (represented by variable resistor 52), and current resistor 50 to complete the circuit. The signal across patient 12 (i.e. variable resistor 52) is amplified by amplifier 42 and separated by separator 34 into EKG and respiration components. Isolation devices 44 and 46 separate patient 12 from the remainder of the circuitry and from earth ground for patient safety. In practice, this function is preferably accomplished by isolation transformers and/or electro optic isolators.

In the actual system, variable resistor 52 consists of conductors 18 and 26, electrodes 16 and 24, and the impedance across the body of patient 12 (see also FIG. 1). It is intended that the variation in resistance of variable resistor 52 be produced primarily by the respiration activity of patient 12, although cardiac artifacts and transient artifacts will also be present as explained above.

Circuit 54 measures the change in voltage drop across variable resistor 52 within the pass band of the respiration monitoring circuitry. This change in voltage drop is proportional to the change in resistance of variable resistor 52 because current resistors 48 and 50, being the only other circuit elements constituting the load, are of constant resistance.

Figure 4:
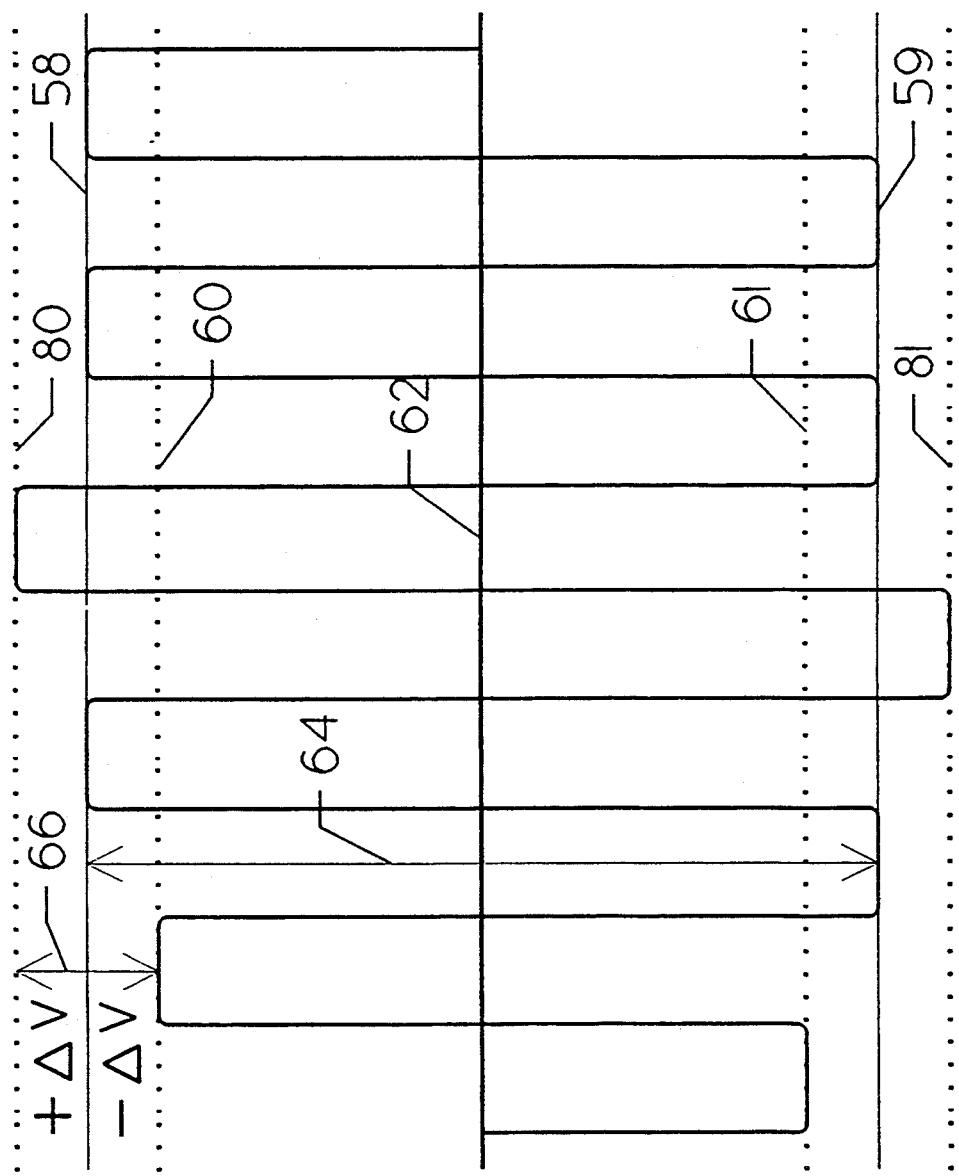
FIG. 4 is a view of the monitoring carrier.

FIG. 4 is a graphical representation of several cycles of the 31.25 khz carrier signal as presented to circuit 54 (see also FIG. 3). This yields a period of 32 microseconds. The square wave of the 31.25 khz carrier signal has a nominal voltage 64 which varies between positive fixed voltage level 58 and negative fixed voltage level 59 on either side of null voltage level 62. Impressed upon the carrier signal is a variable voltage 66, which amplitude modulates the 31.25 khz carrier signal on both sides of null level 62. It is assumed that variable voltage 66 will vary between positive levels 60 and 80 and between negative levels 61 and 81 under normal conditions (i.e. without presence of transient artifacts).

Nominal voltage 64 is a relatively stable component associated with the nominal resistance across patient 12, along with the resistance of the electrodes, conductors, etc. Variable voltage 66 is proportional to the change in resistance across the body of patient 12 over time. A primary component of this resistance change results from respiration activity. However, it also contains components associated with transient artifacts.

Figure 5:
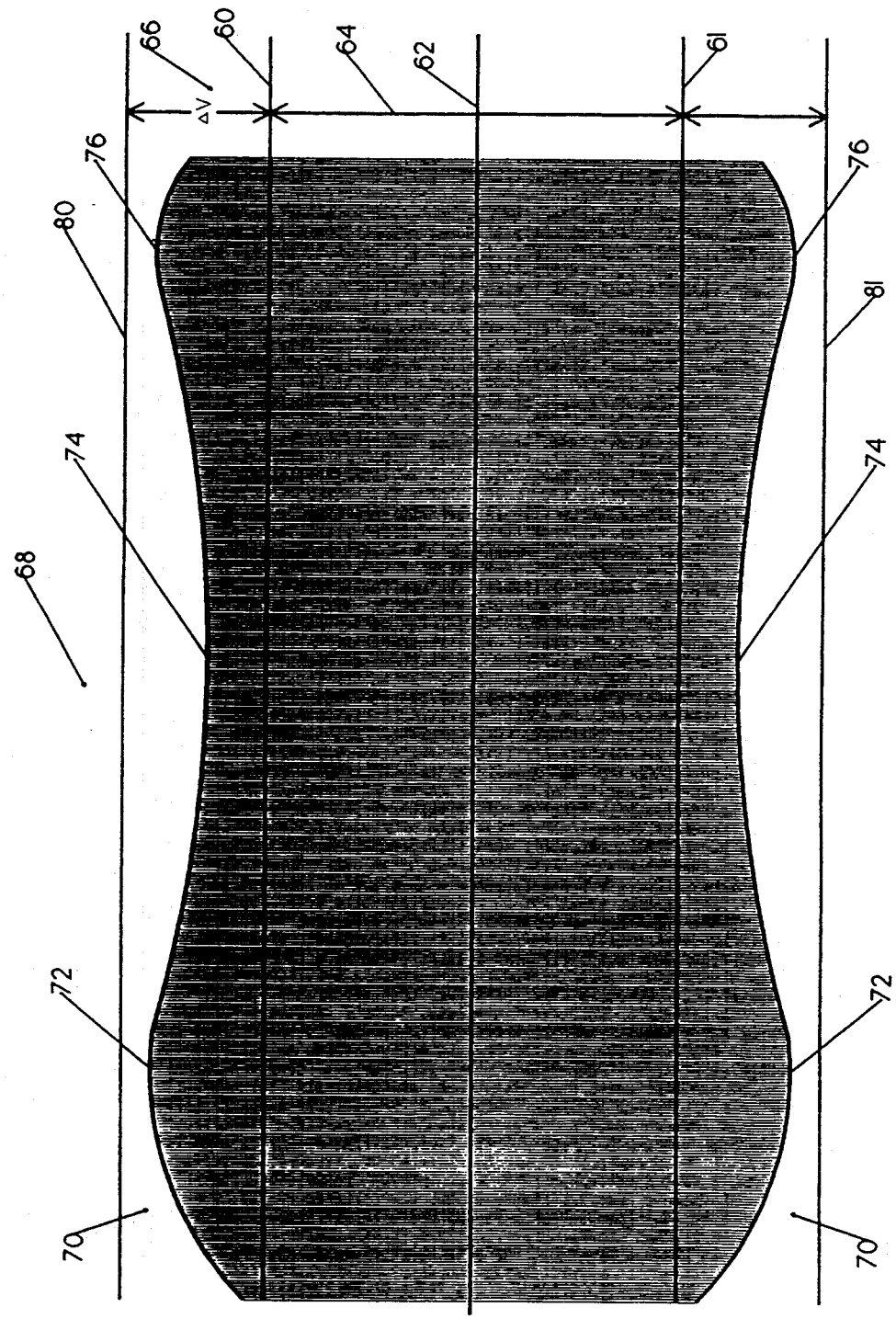
FIG. 5 is a view of the monitoring carrier modulated with a respiration signal.

FIG. 5 is a graphical representation 68 of many cycles of the 31.25 khz carrier signal as modulated by respiration signal 70. Nominal voltage 64 is between fixed voltage levels 60 and 61. Variable voltage 66 varies between voltage levels 60 and 80 in the region positive to null voltage 62 level and between voltage levels 61 and 81 in the region negative to null voltage level 62.

Respiration signal 70 typically has a period of from about one half second up to several seconds measured from peak 72 to trough 74 to peak 76. It can be seen that this signal can be demodulated to obtain the actual respiration signal for monitoring purposes.

Figure 6:
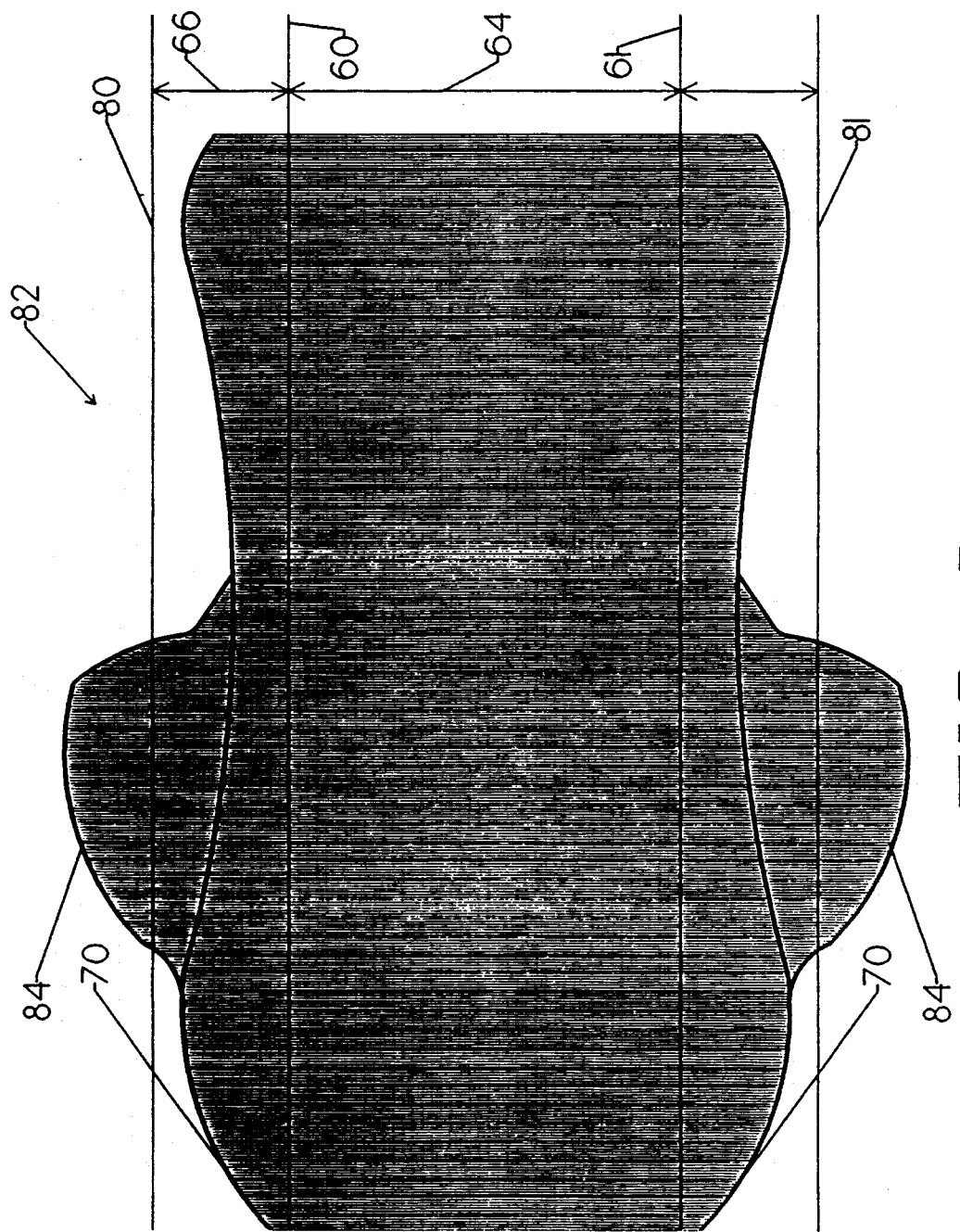
FIG. 6 shows the signal of FIG. 5 as further modulated by a transient artifact.

FIG. 6 is a graphical representation 82 of the respiration monitoring signal of FIG. 5 with a transient artifact signal 84 impressed thereupon. The most immediate problem presented by transient artifact signal 84 is that it exceeds voltage level 80. This means that the signal must be compressed in some fashion to prevent swamping and/or damage to the monitoring circuitry. This could be accomplished by attenuation of the entire signal to vary between voltage levels 80 and 81 using a gain reduction circuit. Unfortunately, this would result in attenuation of respiration signal 70 as well. Such attenuation would likely produce failures to identify actual respiration signals and could produce false alarms.

A second and perhaps more significant problem is that of timing of reduction and restoration of normal system gain. To prevent swamping, the system gain must be reduced before the transient artifact signal is processed. If not, swamping occurs and the system typically requires a substantial time period to recover. Even if the gain is reduced early enough, it must be restored to normal immediately after the transient artifact has passed to prevent loss of subsequent respiration data. Minimization of the time period to recover from a transient artifact is a key aspect of the present invention.

Figure 7:
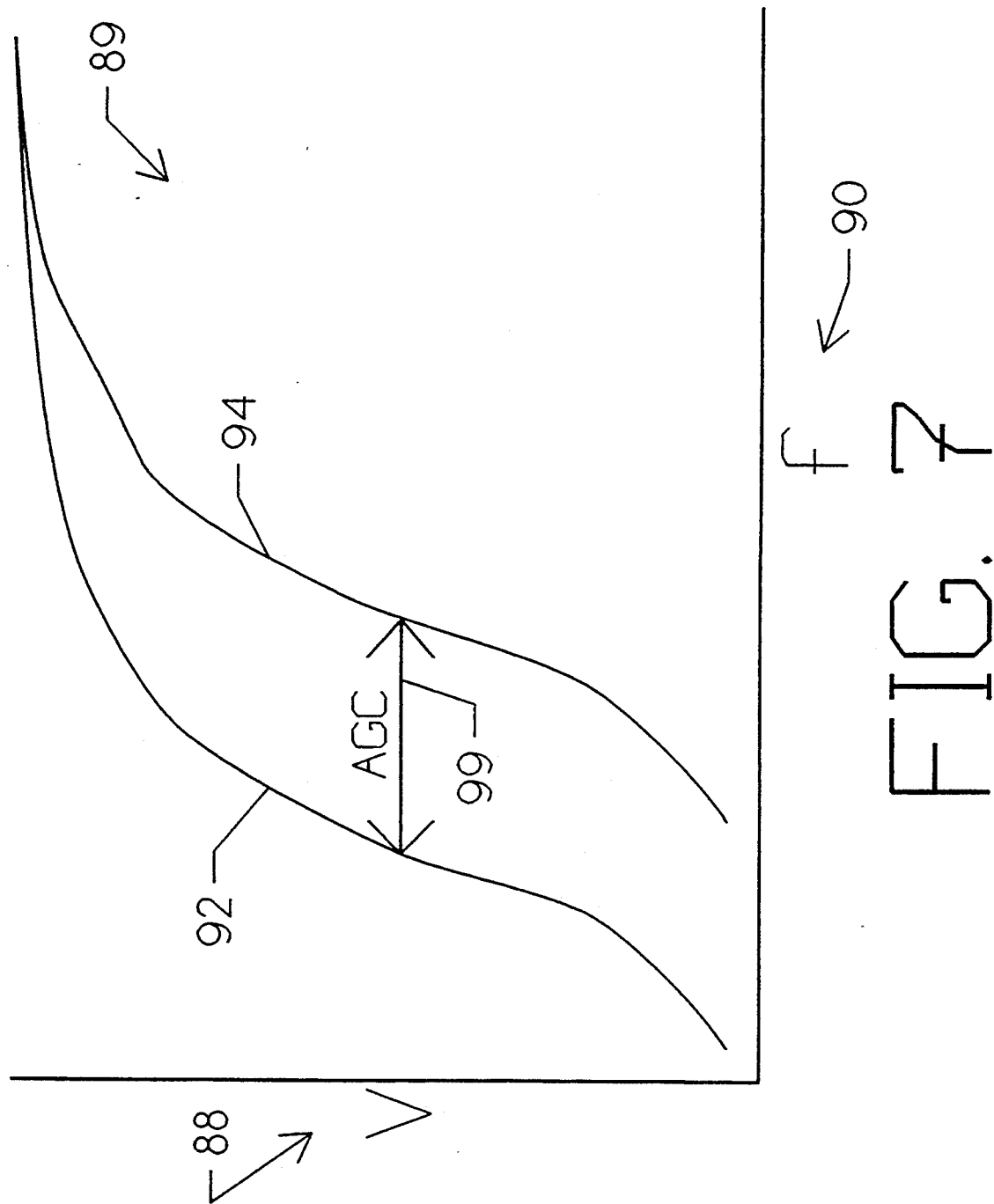
FIG. 7 shows the change of monitor pass band under the presence of a transient artifact.

FIG. 7 is a graphical representation 89 of the operation of the present invention. In accordance with the preferred mode of the invention, the transient artifact signal 84 is accommodated by a change in the pass band of the monitor, during the period of time that the composite signal exceeds voltage level 80 (see also FIG. 6). This provides selective attenuation of the transient artifact signal with much less attenuation of the respiration signal. This is most effective when the frequency of the transient artifact signal is sufficiently different from the frequency of the respiration signal, which is most often the case.

Graphical representation 89 shows voltages 88 plotted as a function of frequencies 90. This is a method of defining the pass band of the circuit. As can be seen, automatic gain control circuit 99 changes the pass band of the circuit from curve 92 to curve 94 as a result of the presence of transient artifact signal 84. This change is reversed immediately after the transient passes, returning the pass band of the system to curve 92. The frequency change means that transient artifact signal 84 is selectively attenuated to a greater degree than respiration signal 70.

Figure 8:
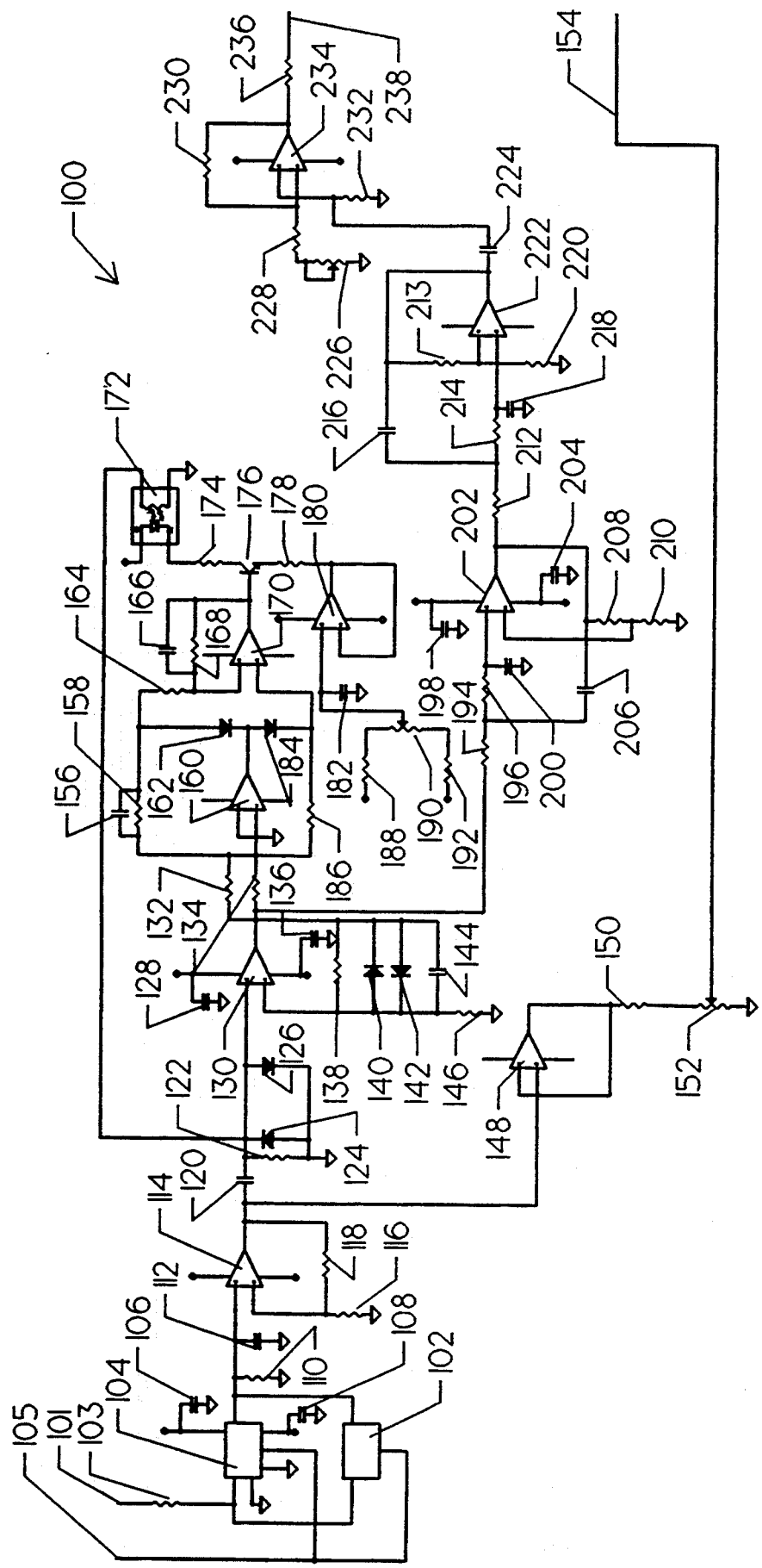
FIG. 8 is a detailed schematic diagram of the transient artifact suppression circuitry.

FIG. 8 is a schematic diagram 100 of the actual means of changing the pass band along with the associated circuitry. After signal separation, the respiration component transferred on cable 38 (see also FIG. 2) is input via line 101. Demodulation of the signal received via input resistor 103 is accomplished by the synchronous rectifier comprising half wave rectifiers 102 and 104. Synchronism with the 31.25 khz oscillator 40 (see also FIG. 3) is provided by line 105. Capacitors 106 and 108 provide suppression of parasitics.

The demodulator operates into load resistor 110 with capacitor 112 removing the remaining higher frequency components. The demodulated signal is normally in the range of 0.5–2.5 hz. This signal is amplified by operational amplifier 114. Gain is supplied by resistors 116 and 118. The signal at that point has a voltage which is proportional to the change in resistance of the system. This signal is amplified by amplifier 148 and supplied through load resistor 150 and output adjustment potentiometer 152 to the digital circuitry of the monitor by line 154 as a signal of 1.7 volts/kohm.

The same output of operational amplifier 114 is coupled to the respiration signal monitoring and automatic gain control circuitry via capacitor 120 and resistor 122, which along with the secondary of photo resistor 172, determine the basic pass band of the monitor. Resistor 122 is fixed thereby adding a fixed component. The resistance of the secondary of photo resistor 172, in parallel with resistor 122, varies in accordance with the description below to adjust the pass band.

The signal is clamped by diodes 124 and 126 to prevent damage as a result transient artifacts of very large amplitude. This signal is amplified by operational amplifier 130, with feedback provided by resistors 138 and 146, and capacitor 144 as clamped by diodes 140 and 142. Operational amplifier 130 is biased by resistor 146 with parasitics suppressed by capacitors 128 and 136.

The output of operational amplifier 130, having its pass band adjusted as described in further detail below. Operational amplifiers 202 and 222, together with capacitors 200, 206, 216, and 218 and resistors 194, 196, 208, 210, 212, 214, 213, and 220, form a low pass filter.

The output of operational amplifier 222 is coupled to operational amplifier 234 by coupling capacitor 224. Fixed bias is supplied by resistor 232 with gain control supplied by fixed resistor 228 and variable resistor 226. Resistor 230 provides the feedback. The output of operational amplifier 234 is coupled via resistor 236 and line 238 to circuitry for the processing of the detected respiration signal.

The remainder of the circuit elements of FIG. 8 are associated with processing of the transient artifact signals to adjust the pass band of the respiration detection circuitry. The output of operational amplifier 130 is coupled via resistors 132 and 134 to operational amplifier 160, which in combination with diodes 162 and 184 and operational amplifier 170, serves as a full wave rectifier. Feed back is supplied by resistors 186 and 164 and by the parallel combinations of resistor 158/capacitor 156 and resistor 168/capacitor 166.

The output of this full wave rectifier (i.e. output of operational amplifier 170) is used to control transistor 176 which is employed as a voltage to current converter. The current path on the output of transistor 176 is through the primary of photo resistor 172, load resistors 174 and 178, and the current adjustment circuit incorporating operational amplifier 180 and the adjustment circuit containing fixed resistors 188 and 192, along with adjustable resistor 190. Capacitor 182 is used for noise filtering. Thus, the current through the primary of photo resistor 172 is a function of the amplitude and frequency of the respiration signal. In this way, the secondary of photo resistor 172 has a resistance which varies to adjust the pass band at the input of operational amplifier 130. As explained above, this input pass band is determined by capacitor 120, fixed resistor 122, and the variable resistance at the secondary of photo resistor 172.

Having thus described the preferred embodiments of the present invention, those of skill in the art will be readily able to apply the teachings found herein to yet other embodiments within the scope of the claims hereto to attached and wherein:

We claim:

1. In an apparatus for monitoring a patient's respiration wherein said apparatus has pass band means for defining a pass band and processing an input signal having a first amplitude, and means responsive to the processed signal for controlling a monitor, the improvement comprising:
   a. means, connected to said pass band means, for modifying said pass band of said apparatus in response to a transient artifact having a second amplitude within the first amplitude of said input signal; and
   b. means for connecting said means for modifying to said pass band means.

2. The improvement of claim 1 wherein said modifying means includes means for selectively attenuating said transient artifact.

3. The improvement of claim 2 wherein said selectively attenuating means further comprises a resistance/capacitance combination having a resistance.

4. The improvement of claim 3 wherein said modifying means further comprises means coupled to said resistance/capacitance combination for varying said resistance in response to said second amplitude of said transient artifact.

5. The improvement of claim 4 wherein said means for varying comprises a photo resistor.

6. An apparatus for measuring a patient's respiration comprising:

a. a plurality of electrodes adopted to be electrically coupled to said patient;
b. an input signal processing circuit, having a pass band, coupled to said plurality of electrodes for processing an input signal;
c. means coupled to said input signal processing circuit for sensing an amplitude of said input signal;
d. means for modifying said pass band; and
e. means, coupling said means for modifying to said means for sensing, for modifying said pass band by decreasing said sensed amplitude to within a predetermined range.

7. An apparatus according to claim 6 wherein said modifying means includes means for attenuating higher frequencies of said pass band in response to increased amplitude of said input signal.

8. An apparatus according to claim 7 further comprising means coupled to said input signal processing circuit for separating said input signal into a respiration signal and a cardiac signal.

9. An apparatus according to claim 8 wherein said modifying means comprises a resistance/capacitance network having a resistance wherein said resistance varies in accordance with a photo resistor.

* * * * *